(12) United States Patent
Mitchell et al.

(10) Patent No.: US 11,585,790 B1
(45) Date of Patent: Feb. 21, 2023

(54) ANALYTICAL HERBICIDE DETECTION TECHNOLOGY

(71) Applicant: Pace Analytical Services, LLC, Minneapolis, MN (US)

(72) Inventors: Johnny Alan Mitchell, Antioch, TN (US); Nic Rasnake, Murfreesboro, TN (US); Leora Loftis, Lebanon, TN (US)

(73) Assignee: Pace Analytical Services, LLC, Minneapolis, MN (US)

( * ) Notice: Subject to any disclaimer, the term of this patent is extended or adjusted under 35 U.S.C. 154(b) by 65 days.

(21) Appl. No.: 17/387,975

(22) Filed: Jul. 28, 2021

Related U.S. Application Data

(60) Provisional application No. 63/059,704, filed on Jul. 31, 2020.

(51) Int. Cl.
    *G01N 30/14* (2006.01)
    *G01N 33/18* (2006.01)
    (Continued)

(52) U.S. Cl.
    CPC ......... *G01N 30/14* (2013.01); *G01N 30/7233* (2013.01); *G01N 33/1826* (2013.01);
    (Continued)

(58) Field of Classification Search
    CPC ............. G01N 30/14; G01N 30/7233; G01N 33/1826; G01N 33/24; G01N 2030/027; G01N 2033/184
    See application file for complete search history.

(56) References Cited

U.S. PATENT DOCUMENTS

| 5,427,955 A | 6/1995 | Shattuck et al. |
|---|---|---|
| 2019/0293667 A1 | 9/2019 | Huang et al. |
| 2020/0025730 A1 | 1/2020 | Alves Pereira et al. |

FOREIGN PATENT DOCUMENTS

| BR | PI1100608 A2 | 6/2015 |
|---|---|---|
| CN | 101629937 A | 1/2010 |

(Continued)

OTHER PUBLICATIONS

Steinborn, Angelika, et al. "Development of a QuEChERS-based method for the simultaneous determination of acidic pesticides, their esters, and conjugates following alkaline hydrolysis." Journal of agricultural and food chemistry 65.6 (2017): 1296-1305. (Year: 2017).*

(Continued)

*Primary Examiner* — Jennifer Wecker
*Assistant Examiner* — Michael Paul Shimek
(74) *Attorney, Agent, or Firm* — Fredrikson & Byron, P.A.

(57) ABSTRACT

A sample may be prepared and then analyzed using a liquid chromatography with tandem mass spectrometry system to determine presence and concentration of herbicide(s) present in the sample. In some examples, the method involves providing a sample containing one or more herbicides and adding a base to the sample. The base may increase the pH of the sample to ≥12, thereby hydrolyzing esters of the one or more herbicides. The method may further involve, subsequent to hydrolyzing the esters of the one or more herbicides, adding an acid to the sample so as to lower the pH of the sample to ≤3. Once prepared, the sample can be injected into a liquid chromatography instrument to separate the herbicide molecules from other molecules present in the sample before being ionized and characterized by mass-to- (Continued)

charge ratio and relative abundance using one or more mass spectrometers.

17 Claims, 1 Drawing Sheet

(51) Int. Cl.
*G01N 30/72* (2006.01)
*G01N 33/24* (2006.01)
*G01N 30/02* (2006.01)
*G01N 30/04* (2006.01)

(52) U.S. Cl.
CPC ....... *G01N 33/24* (2013.01); *G01N 2030/027* (2013.01); *G01N 2033/184* (2013.01)

(56) References Cited

FOREIGN PATENT DOCUMENTS

| | | |
|---|---|---|
| CN | 102353740 B | 7/2014 |
| CN | 104374849 A | 2/2015 |
| CN | 105510498 A | 4/2016 |
| CN | 105628837 A | 6/2016 |
| CN | 106483232 A | 3/2017 |
| CN | 106526018 A | 3/2017 |
| CN | 108732293 A | 11/2018 |
| CN | 108956812 A | 12/2018 |
| CN | 109061007 A | 12/2018 |
| CN | 109813812 A | 5/2019 |
| CN | 110736800 A | 1/2020 |
| JP | 2003098088 A | 4/2003 |
| RU | 2019827 C1 | 9/1994 |
| RU | 2102741 C1 | 1/1998 |

OTHER PUBLICATIONS

Cotterill, "The efficiency of methanol for the extraction of some herbicide residues from soil." Pesticide Science 11.1 (1980), pp. 23-28. Abstract only submitted.

Kim et al. "Determination of chlorinated phenoxy acid and ester herbicides in soil and water by liquid chromatography particle beam mass spectrometry and ultraviolet absorption spectrophotometry." Analytical chemistry 63.8 (1991), pp. 819-823. p. 819 submitted in lieu of abstract.

Lou et al., "Static Subcritical Water Extraction Combined With Anion Exchange Disk Sorption for Determining Chlorinated Acid Herbicides In Soil," Anal. Chem. 72 (2000), pp. 481-488.

Smith, "Esterification of the hydrolysis product of the herbicide dichlorfop-methyl in methanol." Journal of agricultural and food chemistry 24.5 (1976), pp. 1077-1078. p. 1077 submitted in lieu of abstract.

\* cited by examiner

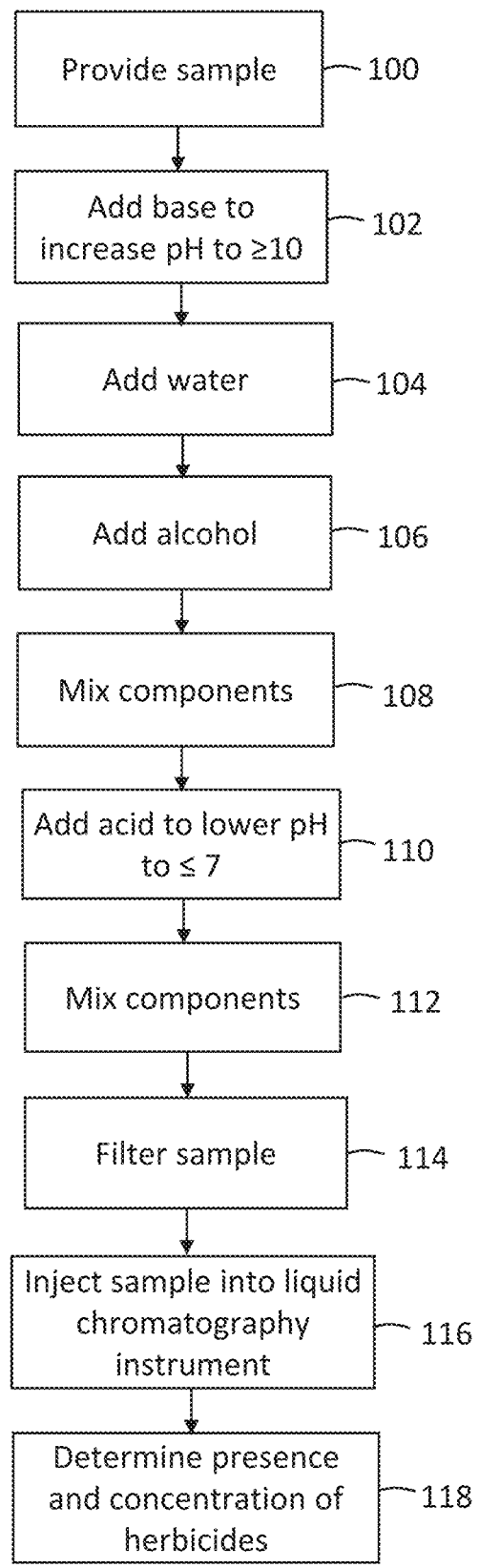

ANALYTICAL HERBICIDE DETECTION TECHNOLOGY

RELATED MATTERS

This application claims the benefit of U.S. Provisional Patent Application No. 63/059,704, filed Jul. 31, 2020, the entire content of which are incorporated herein by reference in its entirety.

TECHNICAL FIELD

The present disclosure generally relates to analytical detection techniques and, more particularly, to analytical detection techniques for determining the concentration of ester-forming herbicides present in a sample.

BACKGROUND

Herbicides are substances used to control unwanted plants. An herbicide can be applied to the soil to be taken up by the root or shoot of emerging seedlings in a preplant or preemergence treatment. An herbicide can also be applied to a portion of the plant above the ground and absorbed by exposed tissues. These are generally postemergence herbicides and can either be translocated throughout the plant or remain at a specific site.

Regardless of the type of herbicide used and the delivery method of the herbicide, residual herbicide may exist after application to the target unwanted plant(s) in the environment where the herbicide was applied. For example, the herbicide may persist in the soil where applied beyond the target application of the herbicide. The herbicide may also transport, e.g., through rain or irrigation, to water sources adjacent the application site.

Analytical techniques may be used to measure the amount of herbicide present in a sample, such as a soil, water, or food sample. Typical analytical techniques for measuring herbicides in samples are time consuming and labor intensive. Moreover, yield losses during the analytical techniques can limit the concentration levels at which an herbicide can be detected in a sample.

SUMMARY

In general, the present disclosure is directed to an analytical technique for quickly and efficiently measuring the amount of herbicide present in a sample under analysis. In some examples, the technique involves obtaining a solid and/or liquid sample having an unknown concentration of an herbicide. The herbicide may be an ester-forming herbicide as opposed to a non-ester-forming herbicide, such as glyphosate. The herbicide present in the sample may be hydrolyzed, e.g., by adding a strong base to the sample, to prepare the sample for subsequent analysis. After preparation, the sample can be analyzed in using a liquid chromatography system, such as a liquid chromatography system with tandem mass spectrometry (LC/MS/MS). The liquid chromatography instrument can separate compounds present within the sample while the mass spectrometer can provide mass to charge ratio data which can help provide structural identity of the compounds present in the sample. In this way, the liquid chromatography with mass spectrometry system can provide a direct measurement of the amount of herbicide present in the sample under analysis.

In some implementations, methods of preparing an herbicide-containing sample for liquid chromatography analysis are disclosed herein. The present methods use a modified hydrolysis reaction coupled with an organic solvent for stability to convert all available herbicide esters to their acid variants. Such methods allow herbicides to be detected quickly and easily at low concentrations, while providing minimal waste.

In one example, a method of preparing an herbicide-containing sample for liquid chromatography analysis is described. The method involves providing a sample containing one or more herbicides and adding a base to the sample so as to increase pH of the sample to ≥12, thereby hydrolyzing esters of the one or more herbicides. The method further involves, subsequent to hydrolyzing the esters of the one or more herbicides, adding an acid to the sample so as to lower the pH of the sample to ≤3 and injecting the sample into a liquid chromatography instrument. The method also includes using the liquid chromatography instrument to measure a concentration of the one or more herbicides contained in the sample.

In yet another example, a method of preparing a sample for liquid chromatography analysis is described. The method involves providing a sample and adding a base to the sample to increase pH of the sample to ≥12. Subsequent to adding the base to the sample, the method involves adding an acid to the sample to lower the pH of the sample to ≤3. The method further involves injecting the sample into a liquid chromatography instrument and using the liquid chromatography instrument to determine presence and concentration of one or more herbicides contained in the sample.

The details of one or more examples are set forth in the description below. Other features, objects, and advantages will be apparent from the description and drawings, and from the claims.

BRIEF DESCRIPTION OF DRAWINGS

FIG. 1 is a flow diagram illustrating an example process for determining the presence and concentration of one or more herbicides present in a sample.

DETAILED DESCRIPTION

The following detailed description is not intended to limit the scope of the invention. Skilled artisans will recognize that the examples provided herein have many useful alternatives that fall within the scope of the invention.

This disclosure relates to methods for determining the presence and concentration of one or more herbicides present in a sample, including techniques for preparing an herbicide-containing sample for liquid chromatography analysis. The present methods allow herbicide levels in the sample to be detected so as to monitor the sample's contamination levels. Such methods can be used, for example, for remediation, screening, and regulatory purposes.

The present methods are beneficial for a variety of reasons. For example, the present methods can detect very low herbicide concentrations and are therefore extremely accurate and precise. In addition, the present methods are environmentally friendly by providing minimal residual waste and eliminating the use of potentially harmful solvents. Furthermore, the present extraction process is faster and less labor-intensive than conventional methods (e.g., enabling the concentration of herbicides in a sample to be detected in as little as 45 minutes).

The present methods involve providing a sample. In many cases, the sample is either a soil sample, a water sample, or a food sample. However, skilled artisans will appreciate that other types of samples can also be tested by the present methods.

In certain embodiments, the sample contains one or more herbicides. In some cases, the herbicides contained in the sample, and measured by the present methods, comprise one or more of $C_3H_4Cl_2O_2$ (Dalapon); $C_8H_6Cl_2O_3$ (Dicamba); $C_8H_6Cl_2O_3$ (2,4-D); $C_9H_9ClO_3$ (MCPA); $C_9H_8Cl_2O_3$ (Dichlorprop); $C_{10}H_{11}ClO_3$ (MCPP); $C_8H_5Cl_3O_3$ (2,4,5-T); $C_9H_7Cl_3O_3$ (2,4,5-TP (Silvex)); $C_{10}H_{10}Cl_2O_3$ (2,4-DB); and $C_{10}H_{12}N_2O_5$ (Dinoseb), including any combinations thereof. However, it will be appreciated that these examples are by no means limiting, and any ester-containing herbicides can be detected by the present methods.

In some embodiments, the sample contains no ester-containing herbicides (i.e., it is devoid of such herbicides). In embodiments of this nature, the present methods can involve verifying that no ester-containing herbicides are present in the sample. In some such cases, the sample may be devoid of all herbicides.

The present methods further comprise adding a base to the sample. Adding the base to the sample causes a hydrolysis reaction to occur (i.e., hydrolyzing esters of the one or more herbicides so as to convert substantially all available herbicide forms, specifically esters, to their acid variant). In some examples, the base is a strong base that completely dissociates in aqueous solution. In some cases, the base comprises sodium hydroxide, potassium hydroxide, or calcium hydroxide, though other strong bases can alternatively be used. In one specific example, the base is sodium hydroxide.

The base may be selected and added to the sample in an amount effective to increase the pH of the sample to a pH greater than or equal to a pH of 10, such as ≥11, ≥11.5, ≥12, ≥12.5, ≥13, or ≥13.5. Increasing the pH of the sample causes the herbicide esters to hydrolyze, allowing the herbicide molecules to be separated and quantified through subsequent analytical processes.

Subsequent to hydrolyzing the esters of the one or more herbicides, the present methods may involve adding an acid to the sample. The acid can be any suitable acid (e.g., a mineral acid and/or an organic acid) that lowers the pH of the sample to a desired level. In certain embodiments, the acid comprises any one of formic acid, hydrochloric acid, sulfuric acid, nitric acid, or perchloric acid. The acid may be selected and added to the sample in an amount effective to reduce the pH of the sample to a pH less than or equal to 7, such as ≤5, ≤4, ≤3.5, ≤3, or ≤2.5.

In general, the lower the pH to which the sample is acidified, the more complete the conversion of herbicide esters to acid form. This, along with other factors described herein, allows the present detection techniques to have excellent precision in measuring herbicide levels. In some implementations, lowering the pH of the sample to a pH of ≤3 helps facilitate measurement of low levels of herbicide in a sample under analysis.

In certain embodiments, the sample is mixed after adding the base, the acid, or both to the sample. Mixing can be performed by various known methods, such as inverting the sample. Inverting the sample can involve inverting the sample multiple times to ensure thorough mixing of the components. For example, in some cases, the sample is inverted 3-5 times after adding the base and is again inverted 3-5 times after adding the acid.

In certain embodiments, the present methods comprise adding water to the sample prior to adding the base to the sample. This may be the case, for example, where the sample is a soil sample. Preferably, after the water is added to the sample, the water and the sample are mixed (e.g., by inverting the mixture multiple times). In some embodiments of this nature, the sample is also mixed after adding the base to the sample and is mixed again after adding the acid to the sample.

Some embodiments further involve adding an organic solvent to the sample after adding the base, but prior to adding the acid, to the sample. The organic solvent may function as a stabilizing agent configured to stabilize the herbicide targets so as to avoid loss of the herbicide targets during the hydrolysis process. In some embodiments, the organic solvent comprises an alcohol (e.g., methanol). This, however, is not required in all embodiments. For example, other water-miscible solvents, other than methanol, can alternatively be used.

In some embodiments, a weight ratio of water to alcohol stabilizing agent ranges from 2:1 water:alcohol to 1:2 water:alcohol, such as a range from 1.2:1 to 1:1.2, or a range of about 1:1. In one embodiment, the alcohol is methanol, and the weight ratio of the water to methanol is about 1:1. After performing various tests, Applicant determined that the mixture of methanol and water provided in a 1:1 ratio was the optimal solvent and ratio to achieve minimal target loss without negatively impacting other target recoveries. In addition to using methanol as the alcohol, in preferred embodiments, the acid is formic acid, the base is potassium hydroxide, and the sample is either a soil sample or a water sample.

Once the sample is prepared in accordance with the steps described above, the sample may be injected into a liquid chromatography instrument for analysis. The liquid chromatography instrument can be any suitable liquid chromatography instrument known in the art. One such instrument is the Agilent 1290 Infinity II LC System, manufactured by Agilent Technologies, Inc. (Santa Clara, Calif., U.S.A.). In some specific examples, the liquid chromatography instrument includes a phenyl-hexyl chromatography column. In other cases, a C18 reversed phase high-performance liquid chromatography (HPLC) column that uses a C18 substance as the stationary phase can be used. While a C-18 column will provide similar data as the phenyl-hexyl column, it is less reliable and less reproducible due to elution issues during the void phase of the chromatography process. Accordingly, a phenyl-hexyl chromatography column may be preferred in certain embodiments.

The liquid chromatography instrument can be used to separate molecules in a liquid mobile phase of the sample using a stationary phase, allowing the concentration of any herbicide(s) present in the sample to be measured directly. Advantageously, this technique enables herbicides to be detected in the sample at low concentration levels.

In certain embodiments, the liquid chromatography instrument uses reverse phase chromatography to measure herbicide(s) in the sample. In some cases, the mobile phase A may be a mixture of water and an organic acid (e.g., water and acetic acid), and the mobile phase B may be a mixture of an organic acid and an organic solvent (e.g., acetic acid and methanol).

In some embodiments, measuring the concentration of the one or more herbicides is performed with mass spectrometry, such as a tandem mass spectrometry. In such cases, liquid chromatographic separation is coupled with tandem mass spectrometry to identify and/or quantify components in the sample. For example, in certain embodiments, the liquid chromatography instrument with tandem mass spectrometer detects the one or more herbicides at concentrations in a range of from 0.5-50 μg/L (e.g., from 0.5-30 μg/L; from 0.5-20 µg/L; from 0.5-10 µg/L; or from 0.5-2 µg/L). In some cases, the liquid chromatography instrument with tandem mass spectrometer detects the one or more herbicides at concentrations in a range of from 5-500 µg/kg (e.g., from 5-250 µg/kg; from 5-150 µg/kg; from 20-75 µg/kg, or even from 5-20 µg/kg). However, certain methods may involve different detection limits depending on need and the instrumentation used.

Skilled artisans will appreciate that tandem mass spectrometry is a technique that uses two or more mass analyzers to break selected ions into fragments. In more detail, tandem mass spectrometry involves first ionizing the molecules of a sample to generate a mixture of ions. Ionization can occur in a variety of ways, e.g., by electrospray ionization, matrix-assisted laser desorption/ionization, or electron ionization. After the molecules are ionized, the ions of a specific mass-to-charge ratio (m/z) are selected and fragmented so as to generate product ions for detection.

Any tandem mass spectrometry instrumentation may be used in the present methods. One suitable example of such instrumentation is the Agilent 6470 LC/TQ Triple Quadrupole LCMS System from Agilent Technologies, Inc. (Santa Clara, Calif., U.S.A.), which uses electrospray ionization analysis.

In certain embodiments, prior to injecting the sample into the liquid chromatography instrument, the resulting sample is filtered. Filtering the sample is beneficial in that it filters out particulates that may interfere with detecting herbicides in the sample. As a result, proper filtering improves sensitivity and provides higher quality detection results.

An example process for determining the presence and concentration of one or more herbicides present in a sample is shown in FIG. 1. The method includes providing a sample (100). In some embodiments, the sample is a water sample, a soil sample, or a food sample. In certain cases, the sample contains one or more ester-containing herbicides.

As shown in FIG. 1, the method can include adding a base to the sample so as to increase pH of the sample to ≥10, such as ≥11, ≥11.5, ≥12, ≥12.5, ≥13, or ≥13.5 (102). In preferred embodiments, adding the base to the sample increases the pH of the sample to a pH of ≥12. The base may be any strong base, such as sodium hydroxide, potassium hydroxide, or calcium hydroxide. In preferred embodiments, the base is potassium hydroxide.

In cases where the sample contains one or more herbicides, adding the base to the sample (i.e., to increase the pH of the sample to ≥10) is configured to hydrolyze esters of the one or more herbicides. As discussed above, this process allows the herbicide molecules to be separated and quantified through subsequent analytical processes. As non-limiting examples, the herbicides contained in the sample can comprise one or more of $C_3H_4Cl_2O_2$ (Dalapon); $C_8H_6Cl_2O_3$ (Dicamba); $C_8H_6Cl_2O_3$ (2,4-D); $C_9H_9ClO_3$ (MCPA); $C_9H_8Cl_2O_3$ (Dichlorprop); $C_{10}H_{11}ClO_3$ (MCPP); $C_8H_5Cl_3O_3$ (2,4,5-T); $C_9H_7Cl_3O_3$ (2,4,5-TP (Silvex)); $C_{10}H_{10}Cl_2O_3$ (2,4-DB); and $C_{10}H_{12}N_2O_5$ (Dinoseb), including any combinations thereof.

The method can optionally involve adding water to the sample (104) (e.g., after adding the base to the sample). Adding water to the sample can be particularly beneficial in embodiments where the sample is not a water sample (e.g., in cases involving a soil sample or a food sample).

The method can optionally involve adding an alcohol to the sample (106). The alcohol may function as a stabilizing agent configured to stabilize the herbicide targets so as to avoid loss of the herbicide targets during the hydrolysis process. In some embodiments, a weight ratio of water to alcohol stabilizing agent ranges from 2:1 water:alcohol to 1:2 water:alcohol, such as a range from 1.2:1 to 1:1.2, or a range of about 1:1. In certain non-limiting embodiments, the organic solvent comprises methanol, and the weight ratio of the water to methanol is about 1:1.

After adding the water and/or alcohol to the sample, the method can optionally involve mixing the components (108). Mixing can be performed by various methods, such as inverting the sample. The sample can be inverted as many times as needed to ensure thorough mixing of components.

Subsequent to adding the base (and optionally, the water and/or alcohol) to the sample, the method further includes adding an acid to the sample so as to reduce the pH of the sample to a pH of less than or equal to 7, such as ≤5, ≤4, ≤3.5, ≤3, or ≤2.5 (110). In preferred embodiments, adding the acid to the sample lowers the pH of the sample to ≤3. The acid can be any suitable acid that allows the sample to achieve the desired pH. In certain non-limiting embodiments, the acid can comprise any one of formic acid, hydrochloric acid, sulfuric acid, nitric acid, or perchloric acid. In preferred embodiments, the acid is formic acid.

After adding the base to the sample, the method can optionally include mixing the components (112). As discussed above, mixing can be performed by any suitable method. In some cases, mixing is performed by inverting the sample one or more times.

After adding the above-described components to the sample, the sample can optionally be filtered (114). Advantageously, filtering allows certain particulates that may otherwise interfere with detecting herbicides to be filtered out of the sample.

After the sample is prepared according to the above-described steps, the sample can be injected into a liquid chromatography instrument (116). The liquid chromatography instrument can help detect the presence and concentration of any herbicides in the sample (118). In more detail, the liquid chromatography instrument can be used to separate molecules in a liquid mobile phase of the sample using a stationary phase, allowing the concentration of any herbicides present in the sample to be measured directly. In some cases, measuring the concentration of the one or more herbicides is performed with mass spectrometry, such as a tandem mass spectrometry. Performing both liquid chromatography and mass spectrometry allows components in the sample to be identified and/or quantified. The liquid chromatography and mass spectrometry instruments can be used to detect the one or more herbicides at concentrations noted elsewhere in this disclosure (e.g., in a range of from 0.5-50 µg/L, or in a range of from 5-500 µg/kg).

Although FIG. 1 shows a particular sequence of steps, skilled artisans will appreciate that the sequence of certain steps in the present methods can be changed without departing from the present disclosure. For example, in certain embodiments, adding water to the sample (104) can occur before or at the same time as adding the base to the sample (102). In certain other cases, adding water to the sample (104) can occur after or at the same time as adding the alcohol to the sample (106). In certain other cases, the base, the water, and the alcohol can be added to the sample simultaneously.

EXAMPLE

Applicant performed various tests in order to develop the present methods. The testing involved using multiple herbicide standards to detect and quantify different herbicide targets present in water samples and soil samples. The specific herbicide targets included $C_3H_4Cl_2O_2$, $C_8H_6Cl_2O_3$, $C_8H_6Cl_2O_3$, $C_9H_9ClO_3$, $C_9H_8Cl_2O_3$, $C_{10}H_{11}ClO_3$, $C_8H_5Cl_3O_3$, $C_9H_7Cl_3O_3$, $C_{10}H_{10}Cl_2O_3$, and $C_{10}H_{12}N_2O_5$.

Each water and soil sample were transferred into a separate vial. Thereafter, herbicide standards and subsequently water were added to each vial. In cases where the sample was a soil sample, the soil was mixed in the vial after the herbicide standards and the water were added thereto. Thereafter, the pH of each sample was adjusted to greater than or equal to 12 using potassium hydroxide as the base. Each sample was then inverted 3-5 times to mix the components, and the sample sediment allowed to settle for 1-2 minutes. Subsequently, methanol was added to each vial as a stabilization agent. Formic acid was then added to each sample to adjust the pH of the sample to less than or equal to 3. Thereafter, each sample was again inverted 3-5 times to ensure proper mixing of components. Finally, a portion of each sample (i.e., an aliquot) was filtered through a polyvinylidene difluoride (PVDF) filter into a different analytical vial. Each processed sample was then injected into the Agilent 1290 Infinity II LC System and the Agilent 6470 LC/TQ Triple Quadrupole LCMS System for liquid chromatography and tandem mass spectrometry analysis of the sample.

Applicant also used matrix spike comparisons with data from the traditional electron capturing detector (ECD) to show that the present methods generate more precise and accurate recoveries of target compounds. Such recoveries are important for maintaining a safe environment.

While some preferred embodiments of the invention have been described, it should be understood that various changes, adaptations and modifications may be made therein without departing from the spirit of the invention and the scope of the appended claims.

The invention claimed is:

1. A method of preparing an herbicide-containing sample for liquid chromatography analysis, the method comprising the following sequential steps:
    providing a sample containing one or more herbicides;
    adding a base to the sample so as to increase pH of the sample to ≥12, thereby hydrolyzing esters of the one or more herbicides;
    subsequent to hydrolyzing the esters of the one or more herbicides, adding an acid to the sample so as to lower the pH of the sample to ≤3;
    injecting the sample into a liquid chromatography instrument; and
    using the liquid chromatography instrument to measure a concentration of the one or more herbicides contained in the sample.

2. The method of claim 1, further comprising adding an alcohol to the sample, wherein the alcohol is added to the sample after adding the base to the sample but prior to adding the acid to the sample.

3. The method of claim 2, further comprising adding water to the sample prior to adding the base to the sample.

4. The method of claim 3, wherein a weight ratio of the water to the alcohol is about 1:1.

5. The method of claim 2, wherein the alcohol comprises methanol.

6. The method of claim 1, wherein the herbicides contained in the sample and measured by the liquid chromatography instrument comprise one or more of $C_3H_4Cl_2O_2$, $C_8H_6Cl_2O_3$, $C_8H_6Cl_2O_3$, $C_9H_9ClO_3$, $C_9H_8Cl_2O_3$, $C_{10}H_{11}ClO_3$, $C_8H_5Cl_3O_3$, $C_9H_7Cl_3O_3$, $C_{10}H_{10}Cl_2O_3$, and $C_{10}H_{12}N_2O_5$.

7. The method of claim 1, wherein the acid comprises formic acid, hydrochloric acid, sulfuric acid, nitric acid, or perchloric acid.

8. The method of claim 1, wherein the base comprises sodium hydroxide, potassium hydroxide, or calcium hydroxide.

9. The method of claim 1, wherein the sample is mixed after adding the base, the acid, or both to the sample.

10. The method of claim 1, wherein after adding the acid to the sample and prior to injecting the sample into the liquid chromatography instrument, the method further comprises filtering the sample.

11. The method of claim 1, wherein the sample is either a soil sample or a water sample.

12. The method of claim 1, wherein the liquid chromatography instrument detects the one or more herbicides at concentrations in a range of 0.5-50 µg/L.

13. The method of claim 1, wherein the liquid chromatography instrument detects the one or more herbicides at concentrations in a range of 5-500 µg/kg.

14. The method of claim 1, wherein measuring the concentration of the one or more herbicides is performed with tandem mass spectrometry.

15. The method of claim 1, further comprising:
    prior to adding the base, mixing the sample with water; and
    filtering the sample after adding the acid to the sample but prior to injecting the sample into the liquid chromatography instrument.

16. The method of claim 15, further comprising mixing the sample both after adding the base and after adding the acid.

17. The method of claim 1, wherein the acid is formic acid, the alcohol is methanol, the base is potassium hydroxide, and the sample is either a soil sample or a water sample.

* * * * *